United States Patent [19]
Bentley et al.

[11] Patent Number: 5,081,106
[45] Date of Patent: Jan. 14, 1992

[54] WOUND DRESSING PROTOCOL UTILIZING COLLAGEN GELATIN FORMED WITH IODINE

[75] Inventors: J. Peter Bentley; Jack H. Fellman, both of Portland, Oreg.

[73] Assignee: The Oregon Health Sciences University, Portland, Oreg.

[21] Appl. No.: 553,979

[22] Filed: Jul. 16, 1990

[51] Int. Cl.⁵ .................. A01N 25/00; A01N 59/22; B01J 37/34; A61F 13/00

[52] U.S. Cl. ........................................ 514/5; 424/443; 424/445; 424/447; 424/668; 424/669; 514/21; 514/944; 514/801

[58] Field of Search ............... 424/443, 445, 446, 447, 424/667, 668; 514/801

[56] References Cited

U.S. PATENT DOCUMENTS

| | | | |
|---|---|---|---|
| 4,347,234 | 8/1982 | Wahlig et al. | 424/15 |
| 4,552,138 | 11/1985 | Hofeditz et al. | 128/156 |
| 4,600,533 | 7/1986 | Chu | 530/356 |
| 4,849,141 | 7/1989 | Fujioka et al. | 264/207 |

OTHER PUBLICATIONS

Bentley et al., *Cosmetic Dermatology* (1986) 1:89–96.

*Primary Examiner*—Frederick E. Waddell
*Assistant Examiner*—T. J. Criares
*Attorney, Agent, or Firm*—Morrison & Foerster

[57] ABSTRACT

A stabilized collagen gel is disclosed as are methods of making this collagen gel which is useful as a wound dressing to prevent dehydration of the subject being treated and infection of the wound. The collagen gel of the invention is stabilized by combining collagen (preferably a pharmaceutical grade collagen, which is atelopeptide collagen), with iodine or a composition capable of generating iodine. The collagen is flowable on first mixing and undergoes a phase transition to form a stable gel with sufficient structural integrity to form a wound dressing.

17 Claims, No Drawings

WOUND DRESSING PROTOCOL UTILIZING COLLAGEN GELATIN FORMED WITH IODINE

GOVERNMENTAL INTEREST

The present invention was developed in part under Federal Government support via contract N00014-84-K-0402 awarded by the Department of the Navy. The United States Government may have certain rights in this invention.

FIELD OF THE INVENTION

The present invention relates generally to wound dressings of the type which include collagen. More particularly, the invention relates to a stabilized form of collagen material which can be used to form a wound dressing composition and to methods of making and using such collagen materials and wound dressings.

BACKGROUND OF THE INVENTION

The ability to maintain an intact outer layer of skin is essential to life itself in that the skin is critical to preventing infection (keeping out unwanted organisms) and preventing dehydration (keeping in desired water and/or bodily fluids). Accordingly, when the skin of an individual is damaged over a large percentage of the individual's body, a life threatening situation arises. The mortality following large burn wounds or other wounds which cause the removal of a large amount of skin are brought about by infection and/or dehydration caused by exposure of large areas of uncovered tissues i.e., tissue material not covered by an outer layer of skin.

In order to prevent dehydration and infection, a primary treatment regime involves the use of dressings which are designed to prevent loss of water and thus alleviate the dehydration problem and simultaneously prevent the proliferation of organisms and thus prevent infections. The dressings may include different forms of antiseptic compounds and may be comprised of a variety of materials capable of preventing the escape of substantial amounts of water.

A second step in a treatment regime requires the application of surgical debridement procedures. In these procedures, badly damaged and dead tissue is removed from the wound area along with any foreign substances which may have become implanted in the exposed tissue. Any such surgical procedures, of course, leave exposed wound areas. Accordingly, a third step in the treatment regime often involves the placement of an auto-graft of the patient's own skin onto the wound bed. Although this procedure can give very desirable results, it is generally not immediately possible in patients where a large percentage of the skin has been burned or removed. Insufficient skin is available in such circumstances and in other situations, the patient may be too ill to undergo the required transplant procedures.

If insufficient skin is available for transplant procedures or the patient is too ill to undergo such procedures, other treatment regimes are available which involve the placement of temporary dressings. Such dressings are comprised of materials such as pig skin, skin taken from human cadavers, various artificial skin-like membranes and various artificial skin-like preparations. These dressings must generally be removed prior to grafting. Further, since they often involve the use of foreign tissue material, they may generate an immune reaction and be rejected. The present invention is an attempt to alleviate and/or eliminate deficiencies of such prior art dressings and thus provide an alternative protocol for the treatment of large surface wounds such as burn wounds.

SUMMARY OF THE INVENTION

The present invention provides a stabilized collagen gel composition containing an anti-bacterial agent. Methods of producing such a stable gel composition as well as methods of forming the composition into wound dressings and using such wound dressings in order to treat large skin wounds such as burn wounds are taught. The wound dressings are useful in preventing dehydration and infection.

The collagen compositions of the invention include a modified form of collagen which is both stabilized and sterilized simultaneously to degrees not possible with other collagen-containing compositions. The collagen is stabilized by combining an atelopeptide or pharmaceutical grade collagen with a reagent capable of generating a stable collagen gel. The reagent must be pharmaceutically acceptable with respect to the wound and compatible with the collagen. The reagent is preferably an iodine generating reagent and most preferably a combination of potassium iodide and potassium iodate in an acidic milieu.

A primary object of the invention is to provide a stabilized form of collagen gel.

Another object of the present invention is to provide a method for producing the stabilized collagen gel material.

Another object of the present invention is to provide a convenient method of stabilizing the collagen composition of the invention by combining water with lyophilized collagen in the presence of an iodine generating system.

An important feature of the present invention is that the stabilized collagen gel compositions can be readily formed into wound dressings useful in the treatment of wounds such as skin wounds such as large burn wounds.

An advantage of the present invention is that after the lyophilized collagen is combined with an iodine generating system, the collagen remains liquid and can be placed and formed into a particular shape on a wound where it begins to set into a firm stable gel. The gelling is accelerated at temperatures of mammalian tissues although it will occur at room temperature if additional time is provided.

A feature of the present invention is that the liberation of iodine in a solution containing atelopeptide collagen causes the collagen to form a firm, stable gel which can be readily utilized in connection with wound healing.

Yet another advantage of the present invention is that the collagen forms a gel which includes the iodine which, in turn, acts as a bactericide when the gel is used in connection with wound healing.

These and other objects, advantages and features of the present invention will become apparent to those persons skilled in the art upon reading the details of the structure, synthesis and usage as more fully set forth below, reference being made to the accompanying examples forming a part hereof.

DETAILED DESCRIPTION OF THE PREFERRED EMBODIMENTS

Before the present stabilized collagen gel compositions and processes for making such are described, it is to be understood that this invention is not limited to the particular collagens, reagents, or process steps described as such compounds and methods may, of course, vary. It is also to be understood that the terminology used herein is for purpose of describing particular embodiments only and is not intended to be limiting since the scope of the present invention will be limited only by the appended claims.

It must be noted that as used in this specification and the appended claims, the singular forms "a," "an" and "the" include plural referents unless the context clearly dictates otherwise. Thus, for example, reference to "a collagen" includes mixtures of collagen materials of the type described herein. Reference to "the method of treatment" includes a plurality of different types of treatment protocols of the type which will be generally known to those skilled in the art or become apparent to them upon reading this disclosure.

The present invention requires the use of collagen material. Initially, the collagen is obtained from a natural source. In that the present invention uss the collagen in combination with a reagent such as an iodine generating reagent which has an antibacterial effect "native" or "natural" collagen can be used in connection with the present invention. The present invention allows the formation of gels useful in wound dressing by starting with all types of collagen material. Accordingly, all types of collagen materials can be used in connection with the present invention. However, the collagen used in connection with the present invention is preferably not "native" or "natural" collagen. It has been modified to some extent in order to purify the collagen material and change its structure in an attempt to eliminate the generation of an immune response when the collagen comes into contact with living tissue. In connection with the present invention, such collagen is generally referred to as "pharmaceutical grade collagen" or "atelopeptide collagen". A general description of collagen and how "native" or "natural" collagen is modified to obtain a pharmaceutical grade collagen is put forth below. Accordingly, the term "pharmaceutical grade collagen" as used in connection with this invention is intended to encompass all types of collagen material which have been modified to some extent in order to purify the collagen material and change its structure in some manner in an attempt to eliminate the generation of an immune response when the collagen comes in contact with living tissue.

In its broadest sense, the present invention is a stabilized collagen gel. The stabilized gel is obtained by combining collagen with iodine or an iodine generating composition and allowing the components to interact until the stable gel is formed. Details with respect to iodine generating compositions, collagens and other components which can be included in the composition are given below. The relative amounts of these components will affect the final composition and the gelling time as further explained below. The following explanation is given with respect to stabilized gels which are most preferably used in connection with wound dressings. However, the stabilized gel composition of the present invention is a novel chemical composition and such a composition is considered to be an important aspect of the present invention apart from any use of the composition as a wound dressing.

Native collagen consists in large part of a triple helical structure containing repeating triplet sequences composed of glycine linked to two additional amino acids, commonly proline and hydroxyproline; thus, glycine appears in every third position in the chain. In addition, all collagen chains contain regions at each end which do not have the triplet glycine sequence and are thus not helical. These regions are thought to be responsible for the immunogenicity associated with most collagen preparations. Immunogenicity can, in large part, be mitigated by removal of these regions to produce "atelopeptide" collagen. This can be accomplished by digestion with proteolytic enzyme such as trypsin, chymotrypsin or pepsin. Because of differing specificities of these proteases, the degree of completeness of removal of the atelopeptides varies. Thus certain proteases, which effect the most complete removal, are preferred. Included among these is pepsin, which results in removal of substantially all of the telopeptide portions.

In native collagen the non-helical telopeptide regions are also responsible for forming the cross-links which aid in stability of the fibrillar structure. These regions contain aldehydes capable of cross-linkage to lysine residues. Atelopeptide collagen does not include any significant degree of cross-linking. Collagen has been subclassified into more than ten types depending on the precise amino acid sequence in the individual chains of the triple helix, the carbohydrate content, and the presence or absence of disulfide cross-linking and other differences. The most common subtypes are Type I which is present in skin, tendon, and bone, and which is made by fibroblasts, and Type III which is found primarily in skin. Other types reside in specialized membranes or cartilage or at cell surfaces. Types I and III contain similar numbers of amino acids in their helices; however, Type III (but not Type I) contains two adjacent cysteines at the C-terminal ends of the triple helix which are capable of forming interchain cross-links. As indicated above, the present invention can be used in connection with all different types of collagen. However, it is most preferably used in connection with atelopeptide Type I collagen which is a "pharmaceutical grade" collagen material which has been purified and modified with respect to the telopeptides in order to eliminate or reduce the generation of an immune response when the collagen comes in contact with living tissue.

Although methods for obtaining collagen from natural sources and treating the collagen to obtain a pharmaceutical grade collagen are not part of this invention, this methodology is described in Example 1 which involves the isolation of collagen from bovine skin. However, the present invention is not limited to this specific example and includes any "Type" of collagen which would be encompassed by the general description of collagen materials given above. Preferred collagens include materials described as "pharmaceutical grade collagen", "atelopeptide collagen" or simply "collagen" throughout this disclosure and the attached claims. A pharmaceutical grade collagen material sold under the tradename "Zyderm" (sold by the Collagen Corporation of Palo Alto, Calif.) could also be used in connection with this invention.

When the collagen is combined with the iodine, it provides a modified collagen composition which is liquid and thus flowable (for a given period of time depending on the amount of iodine added) at room temperature (20° C.-28° C.). The collagen then undergoes a phase transition to create a stable gel. The gel forms in about 10 sec to 10 minutes at room temperature and more rapidly at mammalian body temperature, that is, approximately 37° C. Accordingly, the gel can offer desirable functional properties as a wound dressing.

In a preferred embodiment of the invention, there is provided a Type I pepsin-treated pharmaceutical grade collagen material. The collagen can be substantially dissolved in a slightly acidic aqueous solution such as 0.005M acetic acid. Such a collagen solution may be stored in liquid nitrogen to prevent degradation. The collagen solution can be lyophilized for ease of storage and transportation.

In general, the invention includes a stabilized gel composition which is comprised of a soluble collagen (preferably atelopeptide collagen), water and an iodine generating composition. The iodine-generating composition is present in sufficient amount relative to the collagen so as to promote the formation of a stabilized gel. The collagen has been described above. Further, as indicated above, the water is preferably sterile water. However, due to the antibacterial effect of the iodine, the present invention can be used in combination with nonsterile water which includes bacteria.

The iodine generating composition is basically comprised of an oxidized iodine in combination with a reducing agent at an appropriate pH. The oxidized iodine can be a material such as potassium iodate or iodine pentoxide. Other iodine generating systems can be used with the present invention.

The iodine generating composition can also be formulated in a somewhat different manner. More specifically, it is possible to provide such an iodine generating composition by combining a compound such as an alkali metal iodide with a suitable oxidizing agent such as persulfate, perborate and a additional source of protons such as citric acid. Other oxidizing agents which can be used in connection with the present invention include the following: hydroqen peroxide, tertary butyl peroxide, alkali metal periodate, hypochlorite salts and free hypochlorous acid as well as halogen amines such as chloramine.

The stabilized gel of the present invention is preferably formed by combining collagen with a "iodine generating composition." The use of such iodine generating compositions is the preferred embodiment of the present invention. However, in order to obtain the results of the invention and form the stabilzied gel, all that is necessary is that the collagen be combined with iodine, i.e., iodine in all or any of its forms. Accordingly, iodine as a pure element or in any of its forms can be combined directly or indirectly with collagen in order to form the stabilized gel of the invention. For example, gaseous iodine could be bubbled into a solution of collagen in order to form a stabilzied gel.

USE ADMINISTRATION

The present inventors have carried out studies wherein animals have had applied thereto dressings of gel compositions of the present invention. Such dressings have been found to be well tolerated on open skin wounds. No evidence of an immunological reaction has been seen. It has been found that the presence of iodine in the gel preparations stops the bacterial invasion of the tissue. The ability to leave the dressing in place and the possibility that the dressing will act as an appropriate substrate for the attachment of skin grafts and/or epidermal cells allows healing to begin long before placement of the epidermal graft.

The above description and Example 2 below disclose how to obtain the stabilized form of collagen compositions. These compositions can be readily used as dressings in order to treat large burn wounds or other wounds which cause the removal of large amounts of skin.

WOUND HEALING KITS

The stabilized collagen gel compositions described above can, of course, be used by themselves in order to treat various types of wounds. However, it is preferable to provide additional treating agents in order to improve the effectiveness and convenience of the present invention. Any agents normally used in the treatment of wounds can be combined with the present invention to improve the wound healing effect. This is done by adding such an agent to one or more of a plurality (preferably 3) of separate compartments (preferably plastic blood bag type compartments), each containing different components of the invention which components are combined to form the stabilized gel for treating wounds.

The three compartments will now be described. A first compartment of the kit will include a type I pepsin-treated collagen material, such as the collagen material obtained in accordance with Example 1 below or a commercially available collagen such as Zyderm sold by the Collagen Corporation of Palo Alto, Calif.

The Type I pepsin-treated collagen is dissolved in 0.005M acetic acid for storage in liquid nitrogen. A portion of the collagen solution is mixed with an equal volume of a citrate buffer pH 7.2 and Lyophilized. The collagen is placed in one compartment of a 3-compartment sterile blood bag type container which is then heat sealed. Accordingly, this first compartment includes the collagen component and buffer.

A second compartment of the 3-compartment system contains potassium iodide (KI) and 0.008M citric acid. The citric acid concentration is used to maintain the low pH required for iodine release. There are high concentrations of the buffer component within the collagen compartment. Accordingly, the buffer of the collagen component will make it possible to obtain a substantially neutral pH (in the range of 5.5 to 7.5) when the components are added together. This preparation is then lyophilized and this blood bag compartment is sealed.

The third compartment of the 3-compartment sterile blood bag container contains potassium iodate ($KIO_3$).

Although the above description indicates that the 3 components are separately included within compartments of a 3-compartment blood bag container an alternative approach is possible. In accordance with the alternative, the three substances, collagen, KI and $KIO_3$, are placed in three completely separate containers such as glass ampoules or vials and the components in each of the containers are freeze-dried. The relative concentrations of Collagen, KI and $KIO_3$ which will result in variable gelling times are given in the table shown in Example 2 below.

If the collagen is to be stored in a plastic blood bag, then nitrogen or some inert gas is preferably introduced into the collagen compartment in order to prevent compaction of the collagen during storage and shipment. Compacted lyophilized collagen is considerably more difficult to redissolve than is the original material which is in a somewhat fluffy form.

Regardless of the type of container utilized, it is possible to freeze-dry each of the components within each of the separate containers. This is done in order to reduce weight and provide a more convenient wound healing kit for storage. When the wound healing kit is needed, water is introduced to each of the containers such as by means of a syringe. For example, containers such as by means of a syringe. For example, water is injected into the collagen containing blood bag which is then generally agitated until the collagen takes a solution-like form (usually in a few minutes). The amount of water required to reconstitute the collagen will vary depending on the amount of collagen placed in the bag and the required volume of water should conveniently be premeasured and then added to the bag to provide for accurate measurements. The water is preferably sterile. However, an advantage of the invention is that non-sterile water can be used in an emergency situation due to the anti-bacterial properties of the iodine.

Approximately 60% of the total water to be added is initially inserted into the collagen compartment. After the collagen has been dissolved, the remainder of the water is injected into the KI container in order to dissolve the KI into a solution which is then withdrawn and injected into the $KIO_3$ compartment. Due to the presence of the citric acid in the KI container iodine is rapidly released into the solution. This solution is then withdrawn and injected into the compartment containing the collagen. The seals between the individual blood bag compartments can be designed so that by applying pressure, the interconnecting seals are broken allowing intermixing.

Although the pH of the solution containing the KI and $KIO_3$ is about 3.4 to ensure optimum Iodine release, the pH is rendered substantially neutral by the presence of buffers within the collagen containing compartment which buffers are present in a concentration substantially higher than the citric acid within the original KI compartment.

After the solution containing the KI and $KIO_3$ is mixed with the collagen and agitated, the collagen withdrawn and placed onto a wound area. Additional setting time and body heat from the wound area will cause a firm gel to form (a liquid-to-gel phase transition takes place) with substantial structural integrity thus providing a useful wound dressing with antiseptic capability due to the presence of the iodine.

It is possible for additional antibiotics to be added to the collagen compartment or to the other compartments. For example, an antibiotic such as Gentamicin can be added to the collagen compartment in order to improve the antibacterial effect of the wound dressing while in use. Various growth factors could be added to the kit, included in a separate compartment or added with the water.

The following examples are provided so as to give those of ordinary skill in the art a complete disclosure and description of how to make the collagen compositions and wound dressings of the invention and are not intended to limit the scope of what the inventors regard as their invention. Efforts have been made to ensure accuracy with respect to numbers used (e.g., amounts, temperature, etc.), but some experimental errors and deviations should be accounted for. Unless indicated otherwise, parts are parts by weight, temperature is in degrees Centigrade, and pressure is at or near atmospheric.

Example 1

Extraction of Collagen from Bovine Skin

Fetal calf skin or other bovine skin is obtained from a meat packing plant, stored in the cold room, and shipped on ice. All work in the preparation is done in the cold room at 40° C. The skin is dehaired and all fat and muscle removed. It is then cut into small pieces and then fed into a large meat grinder, using the smallest mesh available. The ground skin is gently shaken for 40 min in phosphate-buffered saline containing 4 grams per liter ethylene-diamine-tetra-acetic acid (EDTA) and 0.05 grams per liter N-ethylmaleimide. After washing, the mixture is centrifuged for 20 min at 4000 rpm and the supernatant discarded. This washing procedure is repeated once more. Following the second wash, the pellet is suspended in 0.5M acetic acid and gently shaken for 1 hr and centrifuged for 20 min at 4000 rpm. This acetic acid can be collected, if required, for the preparation of acetic acid-soluble collagen The pellets are next suspended in 0.5M acetic acid to which is added 2.5 g per liter of pepsin (E.C. No. 3.4.4.1). The mixture is shaken gently overnight, diluted if necessary with 0.5M acetic acid, and centrifuged at 4000 rpm. The supernatants are combined and filtered through gauze. The pellets are resuspended in acetic acid along with additional pepsin, and reincubated at 0° C. for a further 24 hr. After centrifugation the supernatant is filtered and combined with the previous batch; the pellets are then discarded. To the supernatant, NaCl is slowly added over a 2 hr period in order to bring the final concentration to 0.7M NaCl. This precipitates both Type I and Type III collagen, after being allowed to stand overnight. The precipitate is recovered by centrifugation at 5000 rpm for 60 min and the pellet is washed once in 0.7M NaCl containing 0.5M acetic acid. The pellet is then made into a paste with a small amount of 1M NaCl buffered with phosphate to pH 7.5. It is then diluted with a large volume of this buffer and stirred for 48 hr. NaCl is added to the solution to a final concentration of 4M, causing Type III collagen to be precipitated and leaving the Type I collagen in solution. The solution is centrifuged at 22,000 rpm for 1 hr and the supernatant aspirated and saved. Slow addition of NaCl over a 2 hr period to a final concentration of 2.8M causes Type I collagen to be precipitated. After standing overnight the precipitate is recovered by centrifugation at 13,000 rpm for 40 min and the Type I collagen pellet washed with 2.8 M neutral salt solution and recentrifuged. The pellet is suspended in 0.5M acetic acid and stirred until the collagen is dissolved. The solution is centrifuged to remove any undissolved material and the supernatant dialyzed against water until the final concentration of acetic acid inside the dialysis bag is 0.005M. This solution is then assayed for collagen concentration and for the presence of Type III contamination by gel electrophoresis. The purified atelopeptide collagen can then be stored in small batches by freezing and storage in liquid nitrogen.

Example 2

Citrate Buffer

2×sodium citrate buffer (pH 3.4) prepared by mixing 0.2M $Na_2 HPO_4$ and 0.5M citric acid in the ratio of 6.66:1. This is mixed with an equal volume of collagen in 0.005M acetic acid prior to lyophilization.

Iodine Release/Gelling Time
Collagen = 2.5 mg/ml in Na citrate buffer constant.

| $KIO_3$ Conc$^n$ (mM) | KI Conc$^n$ (mM) | I Conc$^n$ (mM) (by Absorbance) | Gelling Time (min.) |
|---|---|---|---|
| 2.24 | 11.25 | 1.07 | 5.0 |
| 4.56 | 22.5 | 1.85 | 4.0 |
| 9.02 | 45.0 | 3.75 | 2.75 |
| 18.0 | 90.0 | 7.5 | 1.5 |
| 36.0 | 180.0 | 14.0 | <1.0 |

The table put forth above can be used in connection with the 3-component kit described above. The approximate gelling time is given for different systems or kits containing different concentrations of the KI and $KIO_3$ components. It should be pointed out that this gelling time is the gelling time required after the components are mixed together within the blood bag. The gelling is accelerated when the composition is placed on the wound and heated.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A collagen gel composition, comprising:
a water soluble collagen material;
water present in sufficient amount relative to the collagen such that the water and collagen form a solution; and
an iodine or iodine-generating composition present in sufficient amount relative to the solution that the solution undergoes a phase transition from the solution to a gel, the phase transition occurring in ten minutes or less at a temperature in the range of 20° C. to 28° C.

2. The composition of claim 1, wherein said iodine generating composition is an oxidized iodine in combination with a reducing agent.

3. The composition of claim 2, wherein said oxidized iodine is selected from the group consisting of alkali metal iodate, periodate and iodine pentoxide.

4. The composition of claim 1, wherein the iodine generating composition includes an acidic pH buffer or other proton source present in sufficient amount to insure iodine release.

5. The composition of claim 1, wherein the soluble collagen is atelopeptide collagen and is present in combination with buffer salts.

6. The composition as claimed in claim 5, wherein the buffer is a citrate/phosphate buffer.

7. The composition of claim 1, wherein said iodine generating composition is a reduced iodine in combination with an oxidizing agent and an additional compound which acts as a source of protons.

8. The composition as claimed in claim 7, wherein the reduced form of iodine is potassium iodide, and the oxidizing agent is selected from the group consisting of persulfates, perborates, hydrogen peroxide, tertary butyl peroxide, alkali metal periodate, hypochlorite salts and free hypochlorous acid and halogen amines.

9. The composition as claimed in claim 8, wherein the source of protons is citric acid.

10. A method of forming a collagen gel, comprising the steps of:
combining collagen and water in relative amounts so as to form an aqueous collagen solution; and
combining a composition capable of generating iodine in solution with the collagen solution in relative amounts so that the solution undergoes a phase transition from the solution to a gel, the phase transition occurring in ten minutes or less at a temperature in the range of 20° C. to 28° C.

11. The method of claim 10, wherein said composition capable of generating iodine is comprised of an oxidized iodine in combination with a reducing agent.

12. The method of claim 10, wherein said oxidized iodine is selected from the group consisting of alkali metal iodate, periodate, iodine pentoxide.

13. The method of claim 10, wherein the composition capable of generating iodine is comprised of a reduced iodine in combination with an oxidizing agent.

14. The method as claimed in claim 13, wherein the reduced iodine is potassium iodide and the oxidizing agent is selecting form the group consisting of persulfates, perborates, hydrogen peroxide, tertary butyl peroxide, alkali metal periodate, hypochlorite salts and free hypochlorous acid and halogen amines.

15. The method as claimed in claim 14, wherein the composition capable of generating iodine is further comprised of a proton donor and the collagen is atelopeptide collagen.

16. The composition as claimed in claim 15, wherein the proton donor is citric acid and the atelopeptide collagen is a pharmaceutical grade Type I collagen.

17. A method of treating a wound, comprising the steps of:
combining collagen and water in relative amounts so as to provide an aqueous collagen solution;
forming a wound-healing composition by combining a composition capable of generating iodine in solution with the collagen solution in relative amounts so that the collagen solution will undergo a phase transition from the solution to a gel which phase transition would occur in ten minutes or less at a temperature in the range of 20° to 28° C.;
applying the wound-healing composition to the wound while the composition is in a solution phase;
allowing the solution to conform to the shape of the wound and undergo the phase transition from solution to gel on the wound.

* * * * *